United States Patent [19]
Jensen

[11] Patent Number: 5,429,592
[45] Date of Patent: Jul. 4, 1995

[54] OCCLUSIVE DRESSING WITH STRIPED PRECUT RELEASE SHEET

[75] Inventor: Ole R. Jensen, River Vale, N.J.

[73] Assignee: Euromed I/S, Fredensborg, Denmark

[21] Appl. No.: 204,753

[22] Filed: Mar. 2, 1994

[51] Int. Cl.⁶ ............................................. A61F 13/02
[52] U.S. Cl. ...................................... 602/59; 602/58; 604/307
[58] Field of Search .................. 602/42, 43, 52, 54, 602/56, 58, 59, 903; 604/307; 428/261

[56] References Cited

U.S. PATENT DOCUMENTS

| | | | |
|---|---|---|---|
| 2,508,855 | 5/1950 | Brown | 428/261 |
| 3,339,546 | 9/1967 | Chen | 128/156 |
| 4,231,369 | 11/1980 | Sorensen et al. | 128/283 |
| 4,245,630 | 1/1981 | Lloyd et al. | 128/155 |
| 4,477,325 | 10/1984 | Osburn | 204/159.12 |
| 4,738,257 | 4/1988 | Meyer et al. | 128/156 |
| 5,000,172 | 3/1991 | Ward | 128/155 |
| 5,160,328 | 11/1991 | Cartmell et al. | 604/307 |
| 5,213,565 | 5/1993 | Rollband | 602/58 |
| 5,267,952 | 12/1993 | Gardner | 602/58 |

*Primary Examiner*—C. Fred Rosenbaum
*Assistant Examiner*—Michael L. Arness
*Attorney, Agent, or Firm*—Tilton Fallon Lungmus

[57] ABSTRACT

An occlusive dressing consisting essentially of a soft, pliant, fluid absorbent and swellable adhesive barrier layer, a thin elastomeric backing layer along one side of the barrier layer, and a removable release sheet covering the opposite skin-contacting surface of the barrier layer. The release sheet is divided into at least two separable sections, adjacent sections being disposed along opposite sides of a predetermined line of separation. Each line of separation is defined by a series of alternating slits and connecting segments with the opposing edges of the slits normally held in contiguous relation by the connecting segments at the ends of the slits. At least one of the sections has a visible locator stripe extending along the line of separation for indicating the location of that line as a user prepares to separate the sections and peel them away from the barrier layer for purposes of applying the dressing.

11 Claims, 1 Drawing Sheet

OCCLUSIVE DRESSING WITH STRIPED PRECUT RELEASE SHEET

BACKGROUND AND SUMMARY

Occlusive and adhesive wound dressings are well known in which the adhesive material takes the form of a pliant water-absorbing, hydrocolloid-containing "barrier" material having both wet and dry tack. The outer surface of the barrier layer is usually covered by a thin backing layer of polymeric film or foam which is preferably highly stretchable so that the backing layer may expand to accommodate the increased volume of the dressing's barrier layer as it absorbs exudate from a wound site. Reference may be had to U.S. Pat. Nos. 4,738,257, 4,477,325, and 4,231,369 for details of wound dressings embodying such features.

The skin-contacting surface of such a barrier layer is normally maintained in clean and sterile condition until application by means of one or more release sheets. Such sheets are commonly formed of siliconized paper and, to facilitate their removal from the barrier layer, are frequently arranged in pairs meeting along one or more lines of separation extending across the dressing. A user simply peels away the release sheets along each line of separation, thereby exposing the barrier surface for application to the wound area.

One disadvantage of such a construction is that the barrier material may be exposed, dry out, and lose its dry tack along the line of separation, even during relatively short periods of storage. Also, the more liquid or semi-liquid constituents of the barrier material (e.g., polyisobutylene) may tend to bleed through the release sheet along the line of separation and, at the very least, cause an unsightly discoloration of the release sheet along that line. Even if the edges of the sheets are carefully positioned so that they are disposed in abuting contact at the time of manufacture, the soft pliant character of the barrier material, and its characteristic ability to swell in the presence of moisture because of its hydrocolloid content, may result in separation of the edges during an interval prior to use. Furthermore, locating the edges in contiguous or abuting relation renders the seam practically invisible, thereby making separation and removal of the release sheets all the more difficult. Thus, if it is possible to maintain the opposing edges of the release sheets in abuting relation prior to use, the removal of those sheets is rendered more difficult and, on the other hand, if such edges are spaced apart during manufacture, or become spaced apart during storage, drying, discoloration and degradation of the barrier material and of the edges of the release sheet may result.

It is therefore an important aspect of this invention to provide a hydrocolloid-type occlusive dressing for the care of skin wounds in which the barrier layer is protected by release sheet means composed of at least two sections meeting along a line of separation. That line is defined by a series of alternating slits and connecting segments. The integral connecting segments join the two sections together and maintain opposing edges of the slits in abuting or contiguous relation until the release sheet sections are removed, at which time the connecting segments become torn or ruptured. Until the segments are so torn, the release sheet sections remain connected and prevent the skin barrier material from drying, discoloring, degrading, and bleeding outwardly along the line of separation.

The sizes of the slits and connecting segments are important because the purpose of the connecting segments is to keep the edges of the release sheet sections in closed condition, despite the pliant character of the adhesive barrier material over which the release sheet sections extend, while at the same time allowing the sections to be peeled away from the barrier layer and away from each other as easily as if such connecting segments were not present. In general, it has been found that the slits should each have a length within the range of about 5 to 25 mm and the connecting segments should each be of a length within the range of about 0.1 to 1.0 mm. Preferred ranges are 6 to 16 mm and 0.3 to 0.7 mm, respectively. When such dimensions are embodied in a paper release sheet covering a pliant barrier layer, it has been found that the connecting segments may be easily torn apart as the release sheet sections are peeled from the barrier layer but, until the time of release sheet removal, the dimensions and spacing of the segments should effectively maintain the slits in closed condition.

Since the slits are normally maintained in closed condition, the actual line of intended separation may not be readily visible to a user. However, at least one of the release sheet sections is provided with a visible locator stripe alongside the line of separation, thereby revealing the location of the line to a user preparing to peel the release sheet sections away from the barrier layer and, as part of the process, to tear or rupture the connecting segments that have maintained the edges of the slits in closed condition.

In manufacture of the product, the release sheet should be slitted and imprinted before being applied to the adhesive surface of the barrier layer. The slitting should constitute a clean cutting operation which forms sharply-cut edges for the slits without displacing or dislodging any appreciable amount of material from the sheet, so that the flexibility of the sheet, which is formed of paper or other easily-tearable material, helps insure that the edges of the slit flex towards an abuting relation after the sheet has advanced past the cutting blade. During the next step in which the slitted and imprinted sheet is applied to the surface of the barrier layer, it is believed that the soft, pliant character of the barrier layer contributes in urging the edges into contiguous relation should such edges have become slightly separated or misaligned following the slitting operation.

Other features, advantages, and objects of the invention will become apparent from the specification and drawings.

DRAWINGS

DETAILED DESCRIPTION OF PREFERRED EMBODIMENTS

Figure 1:
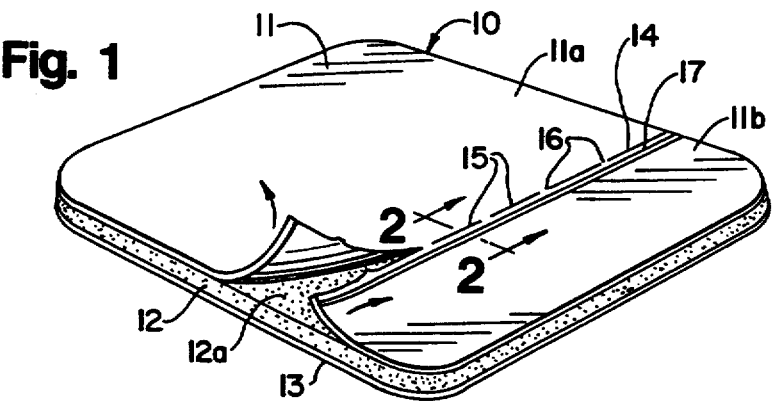
FIG. 1 is a perspective view of a wound dressing embodying the invention, the dressing being shown with corners of the release sheet sections peeled back a short distance for purposes of illustration.
Figure 2:
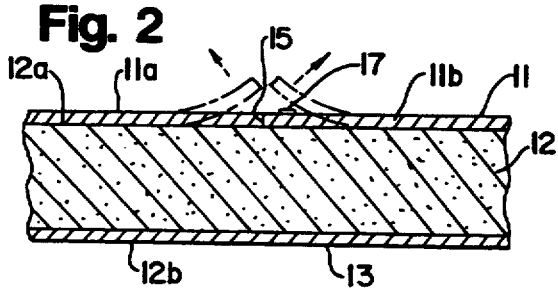
FIG. 2 is an enlarged fragmentary sectional view taken along line 2—2 of FIG. 1.

Referring to the drawings, the numeral 10 generally designates a wound dressing in the form of a generally rectangular pad having rounded or radiused corners. It is to be understood, of course, that the configuration and size of the dressing may vary considerably depending on the particular use for which it is intended.

The dressing is shown in inverted condition to reveal the release sheet 11 covering the surface 12a of adhesive barrier layer 12. Any of a variety of fluid-absorbing hydrocolloid-containing adhesive materials, commonly known as skin barrier materials, may be used for barrier layer 12. One such material is disclosed in U.S. Pat. No. 3,339,546 and comprises a blend of water-absorbing and water-swellable hydrocolloids, such as pectin, gelatin, and carboxymethylcellulose, dispersed in a viscous adhesive substance such as polyisobutylene. Such a composition is pliant and has both wet and dry tack.

Alternatively, the barrier layer may include a cross-linking agent as disclosed in U.S. Pat. Nos. 4,738,257 and 4,477,325. In such a composition, the polyisobutylene, which cannot itself be cross-linked, is blended with a cross-linkable resin to form a continuous elastomeric phase. Copolymer resins formed of ethylene and vinyl acetate (EVA resins) are suitable and can be cross-linked by gamma irradiation.

While the polyisobutylene or other selected elastomer gives the barrier composition its dry tack, it may be desirable to include additional tackifiers for increasing that property. Hydrocarbon tackifiers of the kind described in U.S. Pat. No. 4,231,369 may be utilized. Such a hydrocarbon tackifier may comprise a polymer or copolymer of dicyclopentadiene, alpha-pinene, and/or beta-pinene.

The elastomeric phase may be formulated to contain other polymers such as a styrene-olefin-styrene block copolymer or an ethylenepropylene block copolymer which, although not capable of true cross-linking, may form what has been referred to as "physical" cross links. Such physically cross-linking elastomeric polymers are described in U.S. Pat. No. 4,231,369.

The surface 12b of the barrier layer faces away from the wound when such a dressing is in use and is covered with a thin, elastomeric backing layer 13. A film of polyurethane has been found highly effective, but other polymers having similar properties may be used. Alternatively, the backing layer may be formed of elastomeric foam as brought out in U.S. Pat. No. 4,738,257. In either case, the backing layer should be easily stretchable to accommodate and provide minimal resistance to expansion of the barrier layer when that layer absorbs fluid and swells in use.

Figure 3:
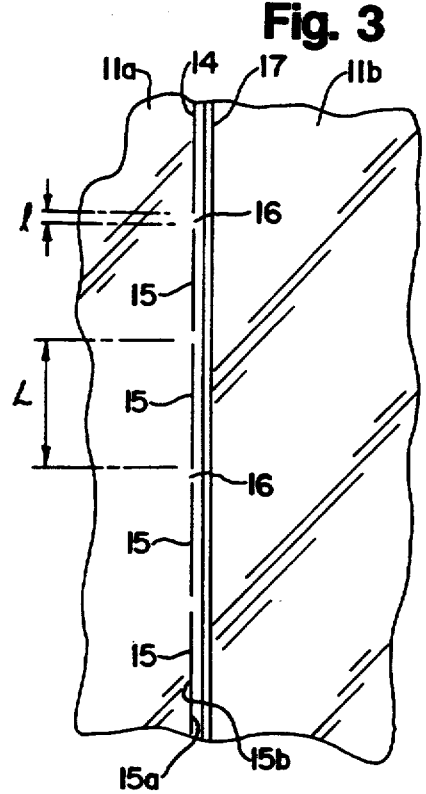
FIG. 3 is an enlarged fragmentary plan view of a portion of the dressing viewed from the release sheet side.

As shown most clearly in FIGS. 1 and 3, a line of separation 14 divides release sheet 11 into sections 11a and 11b. For larger dressings, or dressings of irregular or developed outline, more than one line of separation may be provided, in which case more than two such release sections would of course be provided.

The line of separation 14 is defined by a series of alternating slits 15 and connecting segments 16 disposed in linear alignment. Each of the slits has a length "L" of about 5 to 25 mm, preferably 6 to 16 mm, and each of the connecting segments has a length "l" of about 0.1 to 1.0 mm, preferably 0.3 to 0.7 mm. Particularly effective results have been obtained when the slits are about 10 mm and the connecting segments about 0.5 mm. The relationship is intended to insure that the connecting segments will pose only minimal resistance as the release sheet sections are manually peeled away from each other, and away from the barrier layer, as those segments are ruptured or torn apart as depicted in FIG. 1, and still be effective in containing the edges 15a and 15b of the slits in contiguous relation when the dressing is stored prior to use.

While the slits 15 are clearly visible in the drawing, the fact that their edges are disposed in contiguous relation makes them difficult to see in actual practice. To inform the user of the location of the line of separation 14, a visible indicator stripe 17 is provided by at least one of the release sheet sections 11a, 11b alongside line 14. The stripe is preferably imprinted on the release sheet and is of a color that contrasts sharply with that of a backing sheet. If the backing sheet is of a white or neutral color (as is preferred), then stripe 17 may be red or any other color of the spectrum of sufficient intensity to contrast with the neutral background. The stripe may also be black, although that color is deemed somewhat less effective than others in drawing a user's attention to the imprint as a means for indicating the location of the line of separation.

The release sheet 11 is formed of non-porous non-linting paper or other sheet material that can be easily torn between the fingers. Where paper is used, a coating of silicone or other suitable release agent is provided along the surface of the sheet that contacts barrier layer 12 to prevent the sheet from adhering too securely to the barrier layer. Since release sheets of siliconized paper and other materials are commonly used for wound dressings are well known in the art, further description of their composition and treatment is believed unnecessary herein.

Figure 4:
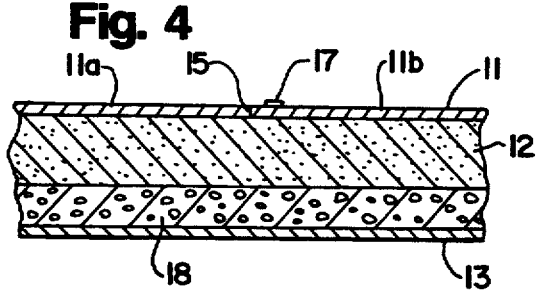
FIG. 4 is an enlarged sectional view similar to FIG. 2 but depicting a second embodiment of the invention.

FIG. 4 depicts an alternative embodiment in which a layer of resilient foam 18 is interposed between barrier layer 12 and backing layer 13. The foam may be either semi-open celled or fully-open celled (fully reticulated), all as well understood in the art.

In making the dressing, release sheet 11 should be cut or slitted and striped prior to application of the sheet material to the surface 12a of barrier layer 12. Application of the precut sheet to the generally planar surface of the barrier layer, preferably in a rolling operation, helps insure that slits 15 are in closed condition at the completion of the manufacturing operation.

While in the foregoing, embodiments of the invention have been disclosed in considerable detail for purposes of illustration, it will be understood by those skilled in the art that many of these details may be varied without departing from the spirit and scope of the invention.

I claim:

1. An occlusive dressing for care of skin wounds, comprising a skin-contacting barrier layer of soft, pliant, fluid-absorbing, swellable, adhesive material; a release sheet of thin, flexible and tearable sheet material removably covering the skin-contacting surface of said barrier layer; and a thin elastomeric backing layer extending along the surface of said barrier layer opposite from said skin-contacting surface, wherein the improvement comprises said release sheet having at least one series of alternating slits and connecting segments extending along a predetermined line of separation and dividing said sheet into separable sections; said sections having opposite edges along said slits normally held in contiguous relation by said connecting segments;

and at least one of said sections having a visible locator stripe extending along said line of separation for indicating the location of said line as a user prepares to tear said sections from each other and peel them away from said barrier layer.

2. The dressing of claim 1 in which said slits each has a length of about 5 to 25 mm and said connecting segments each has a length of about 0.1 to 1.0 mm.

3. The dressing of claim 1 in which each of said slits has a length within the range of about 6 to 16 mm and each of said connecting segments has a length within the range of about 0.3 to 0.7 mm.

4. The dressing of claim 2 in which said slits are about 10 mm in length and said connecting segments are about 0.5 mm in length, measured in the direction of said line of separation.

5. The dressing of claims 1 or 2 in which said release sheet is formed of non-porous paper having an anti-stick coating on the surface thereof in contact with said barrier layer.

6. The dressing of claims 1 or 2 in which said indicator stripe is in the form of a colored line imprinted on one section of said release sheet immediately adjacent said line of separation.

7. The dressing of claims 1 or 2 in which a layer of resilient polymeric foam with either fully-open or semi-open cells is interposed between said barrier layer and said elastomeric backing layer.

8. A method for making an occlusive dressing for care of skin wounds comprising the steps of first forming a series of aligned and interrupted slits in a release sheet to divide said sheet into at least two connected sections separable along a predetermined line of separation and also imprinting said sheet with a visible indicator stripe extending along said line; said slits being formed so that their edges are normally in contiguous relation; and thereafter attaching said release sheet to one side of a barrier layer of soft, pliant, fluid-absorbing and swellable adhesive material.

9. The method of claim 8 in which each of said slits has a length of about 5 to 25 mm, said slits being longitudinally separated by tearable connecting segments each having a length of about 0.1 to 1.0 mm.

10. The method of claim 9 in which each of said slits has a length of about 6 to 16 mm and each of said segments has a length of about 0.3 to 0.7 mm.

11. The method of claim 8 in which said barrier layer of said attaching step has an opposite side backed by a thin backing layer of elastomeric material.

* * * * *